United States Patent [19]

Larsen

[11] Patent Number: 4,926,868

[45] Date of Patent: May 22, 1990

[54] METHOD AND APPARATUS FOR CARDIAC HEMODYNAMIC MONITOR

[76] Inventor: Lawrence E. Larsen, 308 Hamilton Ave., Silver Spring, Md. 20901

[21] Appl. No.: 38,952

[22] Filed: Apr. 15, 1987

[51] Int. Cl.$^5$ ............................................. A61B 5/00
[52] U.S. Cl. ............................... 128/653 R; 128/695; 128/804; 343/700 MS
[58] Field of Search ............... 128/653, 696, 695, 644, 128/804; 343/700 MS

[56] References Cited

U.S. PATENT DOCUMENTS

| 4,360,810 | 11/1982 | Landt | 342/44 |
| 4,572,197 | 2/1986 | Moore et al. | 128/644 |
| 4,600,018 | 7/1986 | James et al. | 343/700 MS |
| 4,638,808 | 1/1987 | Mawhinney | 128/653 |

FOREIGN PATENT DOCUMENTS

| 0099804 | 6/1982 | Japan | 343/700 MS |
| 2165700 | 4/1986 | United Kingdom | 343/700 MS |

OTHER PUBLICATIONS

Iskander et al., "An Electromagnetic Energy Coupler for Medical Applications", Proceedings of the IEEE, vol. 67, No. 10, Oct. 1979, pp. 1463-1465.
Bahl, "A Microstrip Antenna for Medical Applications", IEEE MTT-S International Microwave Symposium Digest, Washington, D.C., U.S.A., (May 28-30, 1980), pp. 358-360.
Pedersen et al., "Microwave Reflection and Transmission Measurements for Pulmonary Diagnosis and Monitoring", IEEE Transactions on Biomedical Eng., vol. BME-25, No. 1, Jan. 1978, pp. 40-48.

*Primary Examiner*—Ruth S. Smith
*Attorney, Agent, or Firm*—Laubscher, Presta & Laubscher

[57] ABSTRACT

A method and apparatus for cardiac hemodynamic monitoring is described. It is based on the complex field amplitudes of microwaves propagated through and scattered by thoracic cardiovascular structures, particularly the heart chambers, as a function of time during the cardiac cycle. Movement artifact and signal leakage are controlled by the use of closely coupled, flexible, light weight, passivated, conformal microstrip antennas that operate in the UHF band. The basic measurement technique is vector network analysis of the power wave scattering parameter in forward scatter configurations of various projections such as posterioanterior (PA), left anterior oblique (LAO), and right anterior oblique (RAO). Non-invasive evaluation of hemodynamic aspects of cardiovascular function is provided. Calibration is possible in human subject without invasive methods.

4 Claims, 5 Drawing Sheets

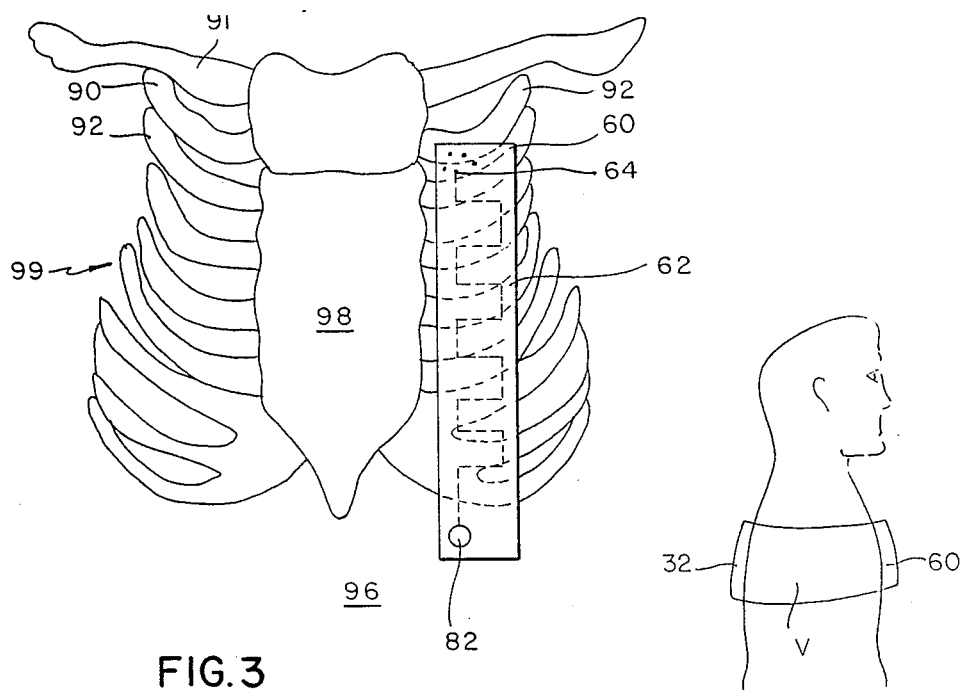
FIG. 3
FIG. 7
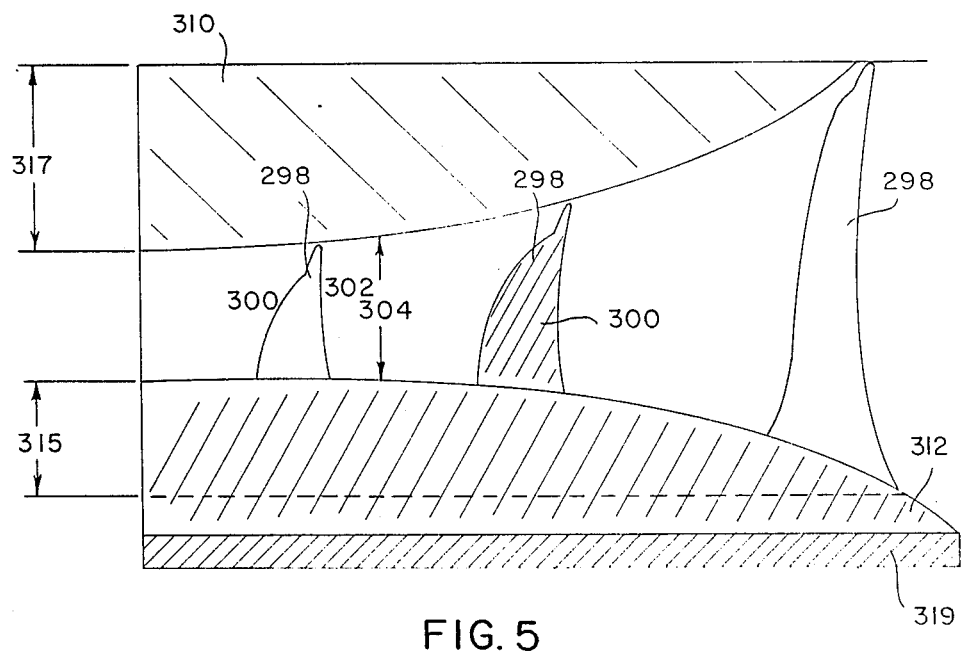
FIG. 5

METHOD AND APPARATUS FOR CARDIAC HEMODYNAMIC MONITOR

FIELD OF THE INVENTION

This invention relates to a method and apparatus for monitoring of the heart. In addition, it serves as a tool for clinical investigation of silent ischemia in ambulatory populations, as a means to evaluate drug treatment response to heart failure, and as a physiologic monitor for the regulation of anesthesia.

The existing methods for functional evaluation in ambulatory populations are based on electrocardiography, but the electrical analogues of cardiac function do not adequately describe the hemodynamic or pumping functions of the heart. The Holter monitor represents an electrical analogue to the expected benefits of this system for the assessment of cardiac pumping functions. Although the Holter monitor is a valuable method, and well suited to telemetric operation, in circumstances where the electrical and hemodynamic functions of the heart are poorly correlated, e.g., inotropic drug effects, and silent ischemia, continuous electrical monitoring often fails to disclose hemodynamic pathophysiology. Additionally, in many instances invasive methods of hemodynamic monitoring are contraindicated.

Presently available methods for measurement of cardiac hemodynamics such as stroke volume are either invasive, or require constant operator intervention. Ionizing radiation is sometimes used. In spite of the generally high risk, the accuracy of invasive methods are no better than plus-and-minus 10% as shown in repeated studies of the same individual in a single cardiac catheterization session. Further, invasive methods are obviously unsuitable for continuous measurement or screening applications.

Noninvasive methods such as gamma camera scintigraphy or ultrasound time-motion and Doppler flow are not suitable for unattended operation in continuous monitoring applications since the positioning of focused transducers is extremely critical and operator interactive. For example, the Doppler method requires measurement of the aortic flow profile just past the aortic valve plus estimation of the vessel cross-sectional area. Ultrasound time motion methods are just as difficult and less accurate due to sampling error. The techniques of two dimensional echocardiography and gamma camera gated blood-pool scintigraphy for estimation of chamber volume have excessive data rates and image processing requirements that are not consistent with mobile operation. Although recent developments in nonimaging radioisotopic systems for ventricular function monitoring do not evidence these problems, ionizing radiation is used, and therefore this procedure is less favorable in a risk/benefit analysis. Secondly, its time domain records of isotope activity are less well correlated with ventricular volume as shown for UHF band insertion loss studies performed in animals. Thirdly, the short half-life needed to reduce risk from the ionizing radiation leads to several operational disadvantages such as a requirement for on-site isotope generation and reinjection of radioisotope after two to four half lives.

BACKGROUND OF THE INVENTION

Prior microwave methods for cardivascular monitoring are based on heart rate detection from Doppler (velocity) processed data in back scatter or narrow angle bistatic geometries. No hemodynamic measures are available. Important improvements in microstrip antenna technologies in the instant invention ameliorate loss of signal with subject movement and interference from unrelated movement or external signal sources that effect sensor operation by way of leakage or fringing fields.

The instant invention for a microwave monitor of cardiac hemodymanics is distinguished from ultrasound systems since it is neither labor intensive nor greatly dependant upon operator skill. These are benefits of the fact that transducer placement is not critical and it is not an imaging method. It is distinguished from radioisotope methods in that neither ionizing radiation nor isotopes are involved and chamber volumes are estimated by changes in forward scattered complex field amplitudes, especially the phase of $S_{21}$. The instant invention is distinguished from other microwave methods in its use of vector processing of coherent forward scattered fields; by the availability of, and processing for, hemodynamic indices rather than simply heart rate; and by antenna technologies that reduce artifact from slippage, leakage and fringing field effects. This ease of use and relatively noncritical antenna positioning combine to produce a robust method for ambulatory monitoring of cardiac hemodynamics that is not available with alternative technologies.

There is no prior art in microwave hemodynamic measurements in humans that uses flexible, closely coupled microstrip antennas and vector processing of the scattered complex field amplitudes.

Past methods used were based on waveguide antennas and scalar processing of forward scattered fields. Past methods, therefore, are insensitive to electrical length(s) of the propagation path and unsuitable for ambulatory use.

Human work is limited to Doppler processing of back scattered or narrow angle bistatic systems. Doppler processing detects the velocity of interfacial movement using a noncontacting wave guide antenna and monostatic Doppler processing of the back scattered field. It does not measure the complex field amplitudes (CFA). Furthermore, there is little or no penetration of the sensor signal beyond the first interface because of the high reflection coefficient from air to chest wall and high carrier frequency (ca 10 GHz) as opposed to the UHF band used by the instant invention needed to allow extraction of Doppler components from the slowly moving chest wall.

Recent heart rate monitors explored several frequencies between 2 and 12 GHz with patch antennas and Doppler processing from monastatic (back scattered) or narrow angle bistatic configurations. The antennas were not in skin contact, but rather placed on top of protective clothing.

Later, two frequencies (X band and S band) were studied in a fully shielded enclosure except for a thick Teflon face on one side. Doppler processing was replaced by detection of oscillator pulling by changes in collector current with load mismatch; but results were unreliable due to signal disruption and nearby, unrelated movement provented successful operation of the sensor. Also, related movement such as that involving the verlying muscle was still more troublesome and the signal was disrupted to the point of becoming unusable. The system was limited to the detection of arterial pulse with later processing for lost beats.

A constant problem with prior designs derives from movement artifact. This has two forms; (1) transducer movement with respect to the target issue whether due to surface slippage, inertial effects, or movement of internal structures; and (2) related movement such as changes in cable capacitance with bending or leakage/-fringe fields leading to interference. The design procedures of prior art did not provide for low profile patch antennas that are closely coupled and conformal. The sensor must be mechanically coupled to the target with a low moment of inertia. Prior art placement of the sensor increased the effective moment of inertia and led to an inability to accomplish constant, close coupling of the sensor to the target.

Additionally, prior techniques failed to provide close electromagnetic coupling because of the thick radome. A thin, conformal radome also decreases leakage effects and fringing fields.

No prior art utilized vector analysis of scattering parmeter $S_{21}$ which provides the advantages of phase information, the advantage of larger radar cross section, and the advantage of contacting microstrip antennas. Furthermore, none of the prior art is suitable for application to ambulatory monitoring.

BIOPHYSICAL BACKGROUND

Biologic dielectrics are characterized by a complex propagation constant that describes material properties with respect to impressed electric fields. It is comprised of a real and imaginary part representing the attenuation constant and phase constant, respectively. The defining equation for the real part, $\alpha$, or the attenuation constant is:

$$\alpha = 1/x(\ln[E_0 E])$$

where x is the propagation distance and E is the original electric field strength. It has the units of Nepers/meter. The imaginary part is the phase constant, $\beta$. Its defining equation is:

$$\beta = pi/\lambda$$

where $\lambda$ is the wavelength. The units are degrees/meter. The complex propagation constant defines the properties of the medium in terms of its microwave constitutive parameters and describes the propagation of plane waves in unbounded dielectric media.

A solution to Maxwell's partial differential equation form for the wave equation is:

$$E = E_0^{j\omega t - \gamma x}$$

where $\gamma$ is the complex propagation constant, $\omega$ is the radial frequency, t is time and x is distance as before. In this way, $\alpha$ may be interpreted as the rate of decay of the envelope of the electromagnetic train as it propagates in the dielectric. $\beta$ is related to the optical concept of the index of refraction of the medium. It is a measure of the retardation of the velocity of propagation $$n = c/v = beta = [\lambda/2n]$$

where n is the index of refraction, c is velocity of the propagation of light or microwaves in a vacuum, and v is the velocity of propagation in the dielectric.

$\alpha$ and $\beta$ may be related to the microwave constitutive parameters of the medium-namely, the relative complex permittivity, K', and the complex permiability.

The complex propagation factors of alpha and beta may be related to the magnitude and phase of scattering parameter $S_{21}$. The scattering parameter $S_{11}$ is more sensitive to the interface formed by electrical impedance discontinuities than is the case for forward scattered fields. Since the interfaces are moving, the time domain behavior of $S_{11}$ is a function of the movement of the interface and the corresponding electrical impedance discontinuity. The magnitude of the power wave reflection co-efficient is a function of the differences of dielectric properties for the two media comprising the interface according to simplified Fresnel equations for the case of normal incidence.

$$R = K'_1 - K'_2 / K'_1 + K'_2$$

where $K'_1$ and $K'_2$ are the relative dielectric constants of the first and second propagation media, respectively.

The propagation constant itself is a time series when $\alpha$ and $\beta$ are themselves functions of time. In fact, the propagation distance, x, is a function of time since the AP thoracic dimensions are modulated by respiration and cardiac volume changes. The bulk microwave constitutive parameters are time dependant since they represent a variable mixture of low loss tissues such as fat with high loss tissues such as blood. The variation is due to the change in dielectric mixture proportions and the separate constitutive parameters due to the change in blood volume with the cardiac cycle. Lichtenecker's logarithmic mixing rule applies as follows:

$$\log[k_m'] = p_1 \log[k_1] + p_2 \log[k_2]$$

Thus, the log of the mixture permittivity is a sum of the log of the components weighted by their respective proportions. In this way the change in permittivity is multiplicative and the proportion is additive in the antilog domain. Based on prior art, an end diastolic left ventricular volume of 125 cc with a k' of 80, a left ventricular muscle volume of 40 cc with a k' of 55; and an end systolic volume of 25 cc with the same muscle volumes and permittivities is assumed, the contrast available for the two mixture conditions will be 73.15 for end diastole and 63.5 for the end systolic condition. The change in permittivity of about 15% corresponds to stroke volume (SV)

$$SV = EDV - ESV$$

where EDV is end diastolic volume and ESV is end systolic volume. A related and useful method of expression is to normalize stroke volume by end diastolic volume to obtain ejection fraction (EF)

$$EF = SV/EDV$$

The predicted changes in complex permittivity as a function of time are a factor of 10 above the accuracy of measurement of scattering parameter $S_{21}$ with the vector network analyzer.

Instrumentation is based on vector processing of coherent forward scattered fields. The central unifying element is the power scattering wave and Poytings vector. Both heterodyne and homodyne receivers for complex field amplitude may be used; but continuous monitoring of hemodynamic functions favors the homodyne method due to lower cost, smaller size, lighter weight levels and sensitivities that are available.

When measuring the power scattering wave, since biological dielectrics are heterogeneous in situ, the transmission loss is a result of reflection at interfaces, polarization loss, diffraction and simple attenuation. Similarly, the phase shift (with a 2 pi ambiguity) represents variation in path length due to scattering mechanisms as well as that due to beta alone.

The scattering parameter most effected by the time dependent blood volume changes is the bistatic scattering parameter $S_{21}$. The monostatic scattering parameter $S_{11}$ is more sensitive to wall perfusion/motion and less sensitive to path length or insertion loss than the bistatic system. Phase information present in the vector fields allows use of both the real and imaginary parts of $S_{21}$ and $S_{11}$, rather than only the modulus as was the case in earlier methods.

The instant invention differs from the conventional instrumentation in several ways. A single frequency source is used, switch selection of the full complement of two port scattering parameters is replaced by separate measurement of the magnitude of the return loss for $S_{11}$ and only $S_{21}$ CFAs are routed to the receiver; the S parameter test set is replaced by a high directivity directional coupler for the bank 900–930 MHz; the calibrated line stretcher is eliminated as the absolute value of the magnitudes and phases of the $S_{21}$ is replaced by the relative values on a beat-to-beat basis in the time domain; and the CFA receiver is designed for substantially single frequency operation, portability, and throughput at physiologic rates with sensitivity and absolute accuracy as minor considerations. With respect to displays, the most pertinent physiologic parameter for cardiac hemodynamic applications is the time domain behavior of $S_{21}$, rather than the frequency domain behavior in conventional network analysis; and finally, the signal processing is not directed toward vector error correction (since relative rather than absolute values are sought). Rather, the signal processing extracts hemodynamic features from the time domain behavior of $S_{21}$.

As further examples of these differences, the output power and frequency of the signal source need not be highly stable, e.g., an LC tuned oscillator is sufficient for a homodyne CFA receiver. The microwave source output power varies with the measurement configuration and receiver sensitivity. In the case of monostatic systems with receivers of $-50$ dBm noise floor, sensor output powers in the range of 0 dBm are adequate. In the case of bistatic configurations with $-60$ dBm noise floors, output powers of 20 dBm are needed. Decreasing the receiver noise with the use of low noise amplifiers reduces sensor power requirements. Given ca 10 mW of incident power and 70 dB of loss, the signal level at the receiver should be ca $-60$ dBm. Operation at 915 MHz improves upon these results by about 10 dB due to the lower attenuation in the UHF band. The homodyne receiver is preceeded by a low noise amplifier. Signal processing extracts hemodynamic data such as the ascending and descending slopes, peak-to-peak amplitudes, and pulse integrals on a beat-to-beat basis.

Signal processing, after the CFAs are available as functions of time, consists of extracting the chronotropic and inotropic features such as heart rate and wave form features, respectively. The former is easily available by zero crossing or threshold detection and counting, but it is of little interest as cardiotachometry alone does not address hemodynamic features. The hemodynamic features are central to measures of iontropic effect. $S_{21}$ is correlated with ventricular volume, based on prior art. Ventricular volume has at least two separable features that correspond to ventricular filling and ventricular ejection. The ascending slope corresponds to chamber filling and the descending slope corresponds to chamber emptying. The wave processing consists of peak-to-peak amplitudes, ascending slopes, descending slopes and pulse integrals. Peak-to-peak amplitudes may be digitally derived by thresholding and window search for zero slopes. Analog peak-to-peak processing may be performed continuously in real time. The more gradual ascending slope and the steeper descending slope correspond to chamber filling and chamber emptying. These functions may be performed by either digital or analog methods. Analog methods are faster and cheaper to implement, but digital processing is more accurate and more easily achieved.

The essence of all CFA receivers is vector processing by a complex ratiometer that describes the target response normalized to the incident signal. The microwave signal is divided into a test and reference channel. The test channel is taken from the receiving antenna placed on the precordium of the subject, while the reference channel is taken from the signal source used to drive the transmitting antenna placed on the back. The reference channel is used to normalize the test channel for transmitter variations. In the case of homodyne systems, the source is the "local oscillator" and source variations are tracked intrinsically. The complex ratio of the test and reference channels represent a physiologically modulated version of source signal after it is propagated through the chest to become the forward scattered field.

The requirements for portability of the CFA receiver leads to a homodyne design as the preferred embodiment, but a heterodyne design may be advantageous in certain cases.

In the case of the instant invention, the preferred embodiment is based on a 4 port homodyne receiver with primary emphasis on the phase of $S_{21}$. The preferred methods of phase comparison are implemented by two types of circuits at UHF frequencies: lumped and distributed. The distributed circuit design is based on transmission line hybrids whereas the lumped circuit design uses transformers. In either case, quadrature mixing is employed to extract the in-phase and in-quadrature components of the forward scattered field. The phase/amplitude reference is supplied by a sample of the forward power from the transmitter. The test signal is the forward scattered field. Either the reference or the test channel is coupled into two balanced mixers via a sum/difference hybrid. The remaining signal is coupled into the remaining input ports of the double balanced mixer by a quadrature hybrid. In both cases, the unused port is terminated in a matched load. The two mixer outputs are voltage proportional to the in phase, $V_I$, and in quadrature, $V_Q$ components $k \cos \theta$ and $k \sin \theta$, respectively. These may be drive a polar display wherein both the vector magnitude, $|S_{21}| = V_I^2 + V_Q^2$, and the vector phase of $S_{21}$, $\theta$ is the arctan $(V_Q/V_I)$. Alternatively, the two outputs may be converted to a phase difference with a DC coupled resolver circuit for display of phase alone in rectangular co-ordinates.

The EKG is a useful adjunct to hemodynamic instrumentation. The EKG provides a timing function that provides not only heart rate, but also the events of ventricular depolarization. The essential characteristics of EKG instrumentation are well known to those skilled in the art.

The microstrip antenna is a critical part of the system since it is the transducer between the subject and the receiver. Its essential characteristics are light weight and conformability for low moment of inertia and close electromagnetic coupling, thin radome/passivation to prevent surface currents and fringing field/leakage effects, polarization control and acceptable impedance match to thoracic structures.

The patch antenna has many virtues due to its suitability for series production based on the photolithographic methods of construction. In the instant invention, these virtues of the antenna are important, but are overwhelmed by the ability to make a nearly conformal antenna to provide a close fit to the chest and back when supported in an equipment vest, and to be of light weight with small volume. The last of these advantages is important not only for portability, but also to insure consistent contact, i.e., close coupling, of the antenna to the chest in the presence of subject movement. Thus, low inertia is a primary design goal. The microstrip UHF design on a substrate of $k'=10.5$, 50 mil thick, 7" long and 2" wide weighs 45 grams with surface launch fee to coax cable.

Patch antennas are characterized by a ground plane with a dielectric upon which a patch radiating element and feed network are preserved after photolithographic etching removes the remainder of the upper conductor. The patch and the ground plane form the boundaries of a thin, dielectrically loaded cavity.

Conscious integration of the feed and antenna aperature is accomplished in a traveling wave antenna. These are also capable of fabrication in microstrip with better impedance match and polarization control over a large aperature than what is possible with thin patches.

Passivation is employed to prevent ionic surface currents. This is accomplished with thin (5 mil) polystyrene or polyethylene sheets enclosing the antenna.

The preferred polarization is vertical whether on the back or precordium. In the PA configuration, a precordial location for the receiving antenna at the left sternal border and centered on the fourth or fifth intercostal space gives the best performance. The transmitting antenna is placed on an anterioposterior line from the receiving antenna and parallel to the spinal column thereby copolarized with the receiver antenna. The antennas should be gradually bent to conform to the contours of the subject. The antennas are passivated by low loss low k' flexible, dielectric sheet such as 10 mil polystyrene.

Measurements of the vector scattering parameters $S_{11}$ and $S_{21}$ were made at 915 MHz in human volunteers.

Vector measurements in the bistatic configuration disclosed the importance of antenna polarization/placement and provided confirmation of the importance of the phase of $S_{21}$, as well as needed transmitter power vis a vis the receiver noise floor. Microstrip antennas were used. Cross polarization of the transmitting and receiving antennas disclosed depolarization. Small changes in the copolarized magnitude of $S_{21}$, in the order of 1 dB peak-to-peak over the cardiac cycle were observed with the recommended antenna placement. The copolarized phase of $S_{21}$, however, is a far mor robust parameter with peak-to-peak changes of nearly 30 degrees over the cardiac cycle using the same antenna placement. The phase change also was less corrupted by breathing when a simple two pole high pass filter at 0.5 Hz was used.

Vector measurements in the monostatic configuration disclosed the importance of antenna polarization with respect to mediastinal structures and provided confirmation of usage guidelines with respect to antenna placement and transmitter power vis a vis the receiver noise floor. The peak-to-peak excursion in magnitude of $S_{11}$ was less than ¼ dB and very susceptible to noise from breathing. The use of simple high pass filtering was not effective in suppression of respiration signals in the amplitude channel, but it did produce benefit in the phase channel. Peak-to-peak changes in the phase of $S_{11}$ was also more susceptible to breathing artifact than was the phase of $S_{21}$.

These results tend to confirm the analysis performed in the section on dielectric analysis of mediastinal structures. Vector analysis does provide useful, additional information of phase angle as well as magnitude of the insertion loss. The information on electrical path length provided by the phase data provides discrimination of multiple scattering. Vector analysis assists the extraction of hemodynamic indices since electrical path length emphasizes the real part of the complex permittivity whereas the imaginary part is emphasized in attenuation measurements.

SUMMARY OF THE INVENTION

This invention provides a method and apparatus for cardiac hemodynamic monitoring which includes portable UHF receivers, transmitters, and flexible antennas utilizing noninvasive means for detecting cardiac hemodynamic properties through microwave propagation.

A further objective of this invention is to provide values of the magnitude of the power scattering wave parameter $S_{21}$, and the phase angle of $S_{21}$, as a function of time on a heartbeat by heartbeat basis to determine heart stroke volume, diastolic reserve, systolic reserve, chamber filling rate and chamber emptying rate.

Further objectives and advantages of this invention will become more apparent in light of the following drawings and description of the preferred embodiments of the invention.

BRIEF DESCRIPTIONS OF THE DRAWINGS

FIGS. 1a, 1b and 1c are the top, side and cross-section views, respectively, of the preferred embodiment of the invention showing a patch transmitting antenna;

FIGS. 2a, 2b, 2c, and 2d are the top, side, cross-section, conductor views, respectively, of one configuration of the preferred embodiment of the invention showing traveling wave receiving antenna;

FIG. 3 is a perspective which illustrates the placement of the receiving antenna for the preferred embodiment of the invention;

FIG. 5 is a graphic illustration of the ventricular volume on a pulse by pulse basis under stress conditions;

FIG. 7 is an illustration of the vest for mounting the transmitting and receiving antennas on a patient.

DETAIL DESCRIPTION OF THE PREFERRED EMBODIMENTS OF THE INVENTION

Figure 1A:
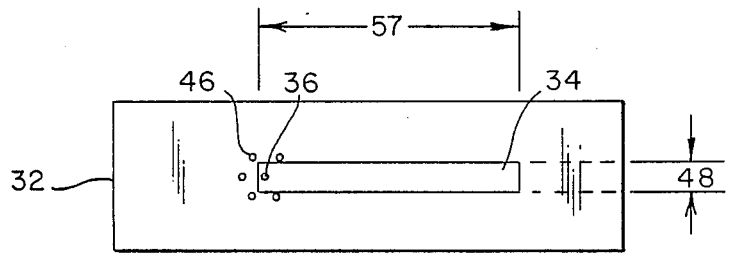
Figure 1B:
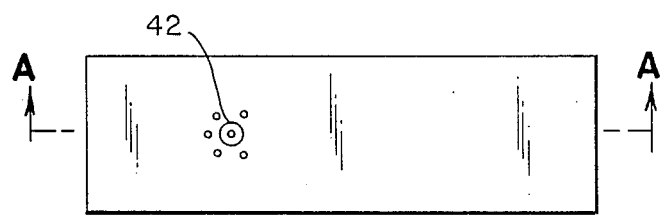
Figure 1C:
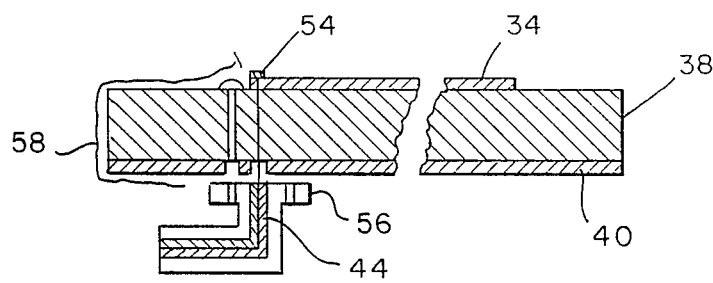
Figure 2A:
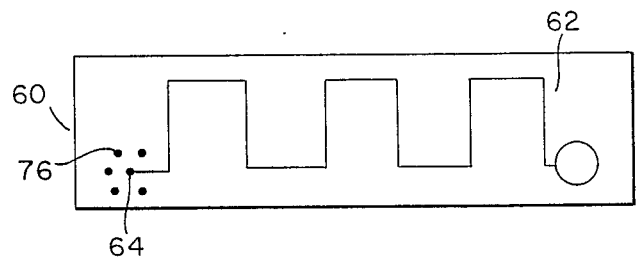
Figure 2B:
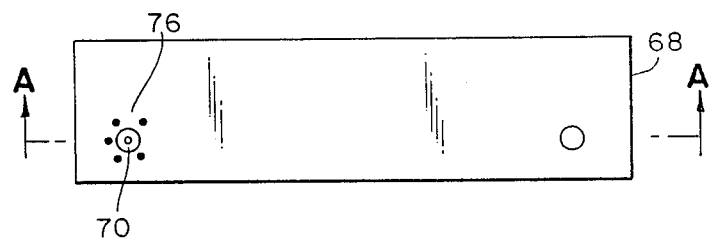
Figure 2C:
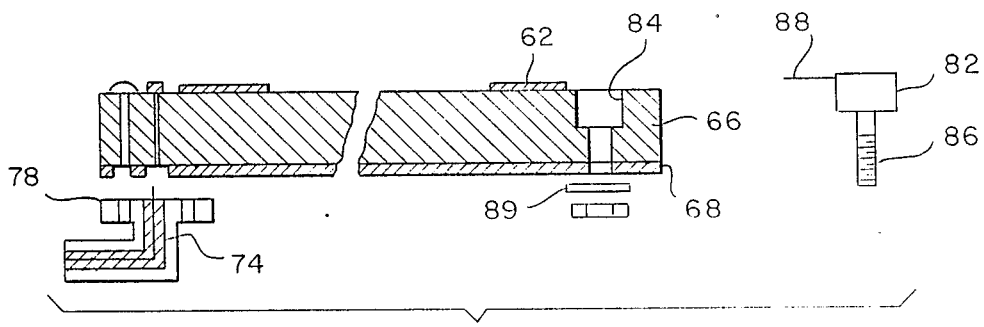
Figure 2D:
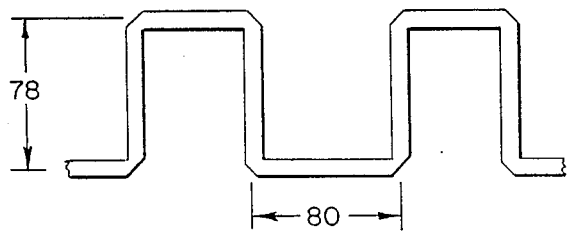

Referring to the drawings, FIGS. 1a-1c generally depict a typical transmitting antenna 32. It is comprised of a thin patch radiator 34, a surface launch feed 36, a flexible dielectric (nominal k'=10.5) substrate material 38, and a ground plane 40. The ground plane 40 is removed in a circular opening 42, concentric with the inner conductor of the coax feed. The circle is not smaller than the diameter of the insulation material 44 of the coax feed. The bolt pattern 46 serves not only the purpose of mechanical attachment to the flange 56 of the surface launcher 36, but also to control mode structure in the dielectric substrate 38 of the antenna. The exact position of the feed point 36 made by the noncaptured center conductor pin 54, on the patch 34 is used to tune the antenna to the feed. The width 48 of the patch is based on the effective dielectric constant of the dielectric substrate. The target value of impedance of the patch is 50 ohms and its length, 57, is one half wave in the dielectric. This places the peak of the electric field in the center of the patch. The antenna 32 is passivated by a thin coating 58 of dielectric material.

In FIG. 2a–2d, the receiving antenna 60 is comprised of a thin traveling wave microstrip antenna 62, a surface launch feed 64, a flexible dielectric substrate material 66, and a ground plane 68. The ground plane 68 is removed in a circular opening 70 concentric with the inner conductor of the coax feed. The opening 70 is not smaller than the diameter of the insulation material 74 of the coax feed cable since the dielectric constant of substrate 66 is greater than that of the insulation material 74. The bolt pattern 76 serves not only the purpose of mechanical attachment to the flange 78 of the surface launcher, but also to control mode structure in the dielectric substrate 66 of the antenna 60. The conductor pattern 62 is a 50 ohm rampart line with the length 80 and width of the steps equal to one quarter wavelength in the effective dielectric constant of the substrate 66. The corners of the line 62 are mitered to 45 degrees. This, in combination with the step dimensions 78 and 80, produce a vertically polarized pattern. The line 62 is terminated in a microstrip load 82 which is counter sunk 84 into the substrate material 66. The load is attached to the line 62 by means of the tab 88 of matching width. The load 82 is grounded by means of a stud 86 extending through the substrate material 66 to be mechanically fixed to the ground plane 68 via a nut and lock washer 89. The transmitting antenna is placed to the left of the spinal column in line with the receiving antenna 60.

Referring to FIG. 3, the recommended placement of the receiving antenna 60 for the posterioanterior projection is shown. The feed point 64 of the line 62 is at the intercostal space between the first rib 90 and the second rib 92. The termination 82 is generally over the epigastrium 96. The antenna 60 is placed off the left lateral margin of the sternum 98 and vertically copolarized to the transmitting antenna, i.e., cross polarized with the rib cage 99.

Figure 4:
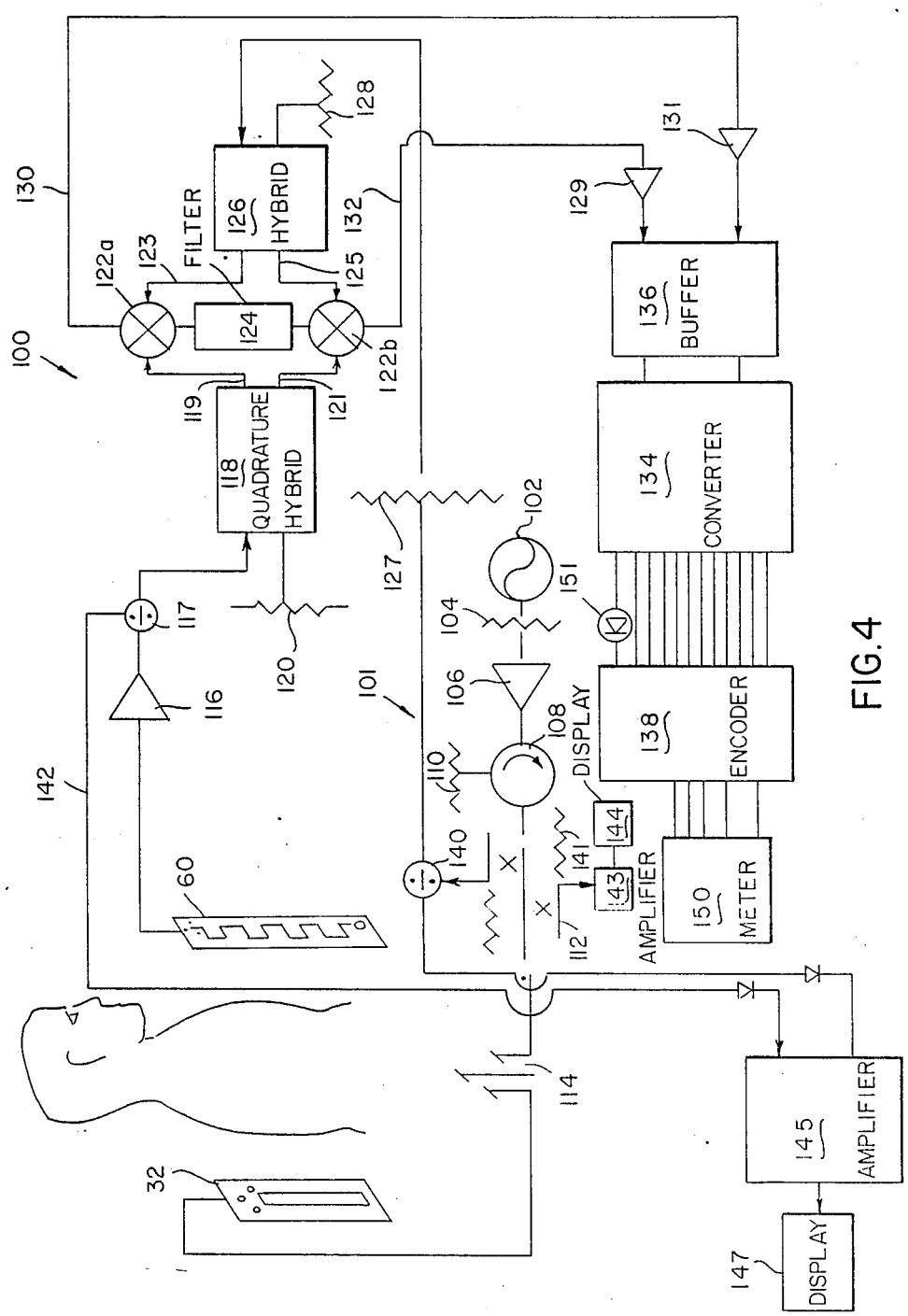
FIG. 4 is a functional block diagram of the preferred embodiment of the four port hemodyne receiver.

In FIG. 4, the preferred embodiment of the four port homodyne receiver 100 is depicted. The transmitting antenna 32 and receiving antenna 60 are shown in the PA projection. The antennas are connected with a vest V worn by the patient as shown in FIG. 7. The transmitter 101 is comprised of a nominal 10 milliwatt oscillator 102, a level set attenuator 104, and a medium power amplifier 106 with 20 dB gain and output power of 20 DBm. A circulator 108 and a load 110 are included to prevent damage to the transmitter if the antenna is not closely coupled with the subject. A reflectometer 112 is used to measure the magnitude of $S_{11}$ to guide operation of a tuner 114 such that a 10 to 20 db return loss is achieved. Detected samples of the incident 140 and reflected power 141 are processed in a log ratio amplifier 143 to display the magnitude of $S_{11}$ on a display 144. The receiving antenna 60 is vertically placed on the left precordium as in FIG. 3. Its output is amplified by a low noise amplifier 116 of nominal 10 dB gain. The amplified forward scattered field is reactively divided by divider 117 to the receiver and the log magnitude $S_{21}$. The receiver begins with a high isolated quadrature hybrid 118, the unused port of which is terminated in a matched load 120. The zero and 90 degree phase shifted outputs 119 and 121 of the quadrature hybrid 118 are applied to the RF ports of two balanced mixers 122a and 122b with DC coupled intermediate frequency ports (IF) lines 130 and 132. Mixer spurious response are terminated in a diplex-type filter 124. The "local oscillator" or reference inputs 123 and 125 to the two mixers 122a and 122 b is supplied by a 0/180 hybrid 126 the unused port of which is terminate in a matched load 128. The level to hybrid 126 is set by attenuator 127. Input to 0/180 degree hybrid 126 is a sample of the forward power 140 used to drive the transmitting antenna 32. This provides a phase and amplitude reference for the receiver. The outputs 130 and 132 are suitably amplified 129 and 131 prior to input buffer 136. The two outputs 130 and 132 proportional to sin and cos $\theta$, respectively, are DC levels proportional to the in phase and in quadrature (sine and cosine) components of the forward scattered field. The magnitude may be taken from detected samples of the incident 140 and transmitted powers 142 and detected then log ratio amplified in 145 for display of the magnitude of $S_{21}$ by 147. The phase of $S_{21}$ is determined by the use of a DC coupled resolver to digital converter 134 after input buffering 136 and displayed on digital meter 150 after binary to BCD encoding 138. An indicator display is based on light emitting diodes 151 in each output line of the converter 134. The LEDs are in order from least significant bit, 0.0879 degrees, to the most significant bit, 180 degrees. Thus, the length of the light string in bit order gives a bar graph type of display that is intuitively interpretable.

Conventional instrumentation for the measurement of scattering parameters consists of the signal source subsection and, the vector network analyzer or complex field amplitude (CFA) receiver. The interface between the two is the S parameter test set. The S parameter test set serves as a broad band RF power divider, directional coupler, line stretcher and double pole coaxial RF switch to allow remote selection of $S_{11}$ or $S_{21}$.

In FIG. 5, a plot of the ventricular volume 298 on a pulse by pulse basis is shown. Conditions of sympathetic stimulation and/or parasympathetic inhibition are present. The ventricular stroke volume 304 is increased due to both diastolic reserve 310 and systolic reserve 312. The features extracted in the signal processing steps are as follows:

Peak-to-peak amplitude 304, filling rate 300, ejection rate 302 and integral (shown by the shaded area) 306. The difference 317 is a stimulation response drawing upon the diastolic reserve 310. The difference 315 is a stimulation response drawing upon the systolic reserve 312. The residual volume 314 is systolic reserve not available to increase stroke output.

Figure 6:
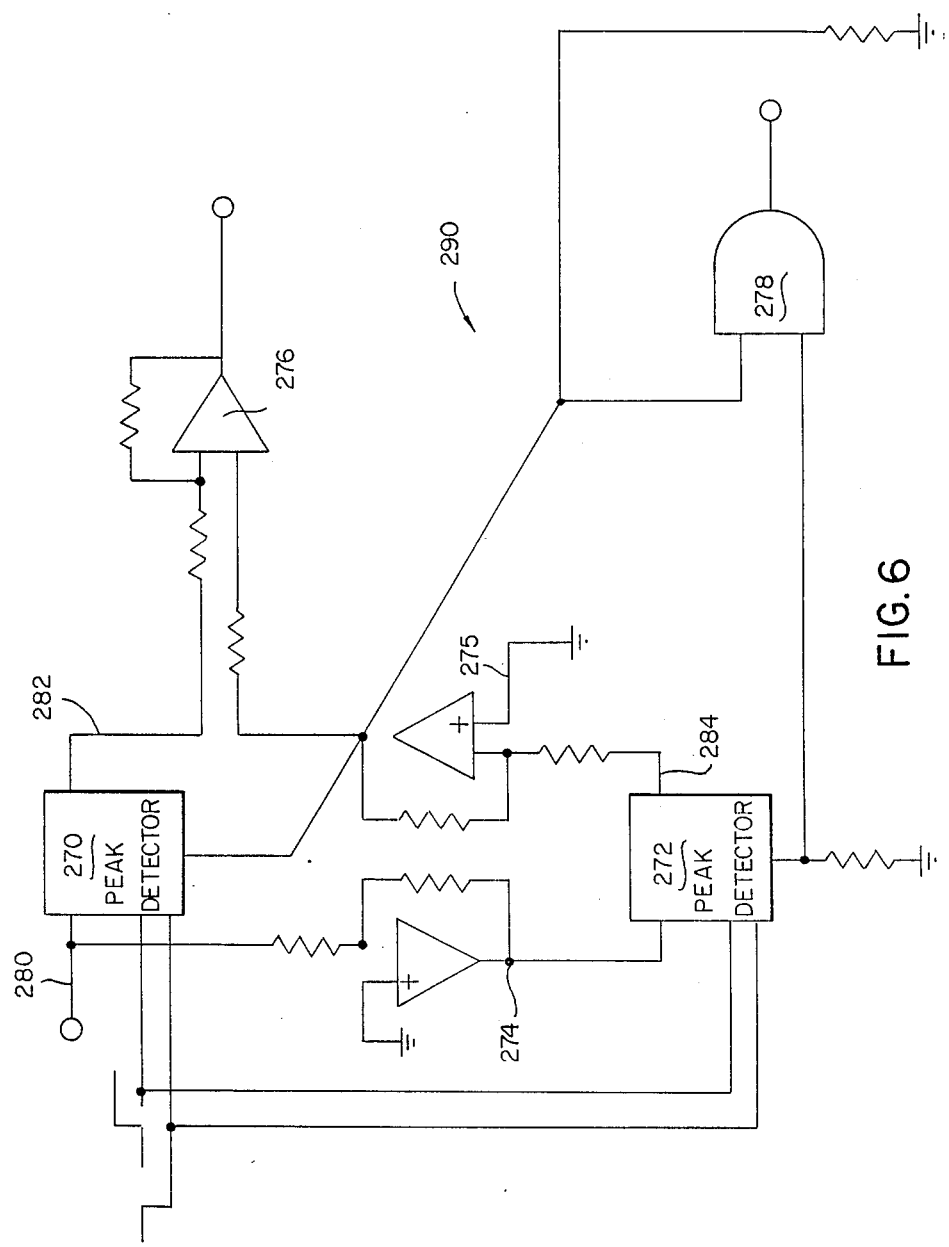
FIG. 6 is a circuit topology for analog peak-to-peak detection of the detected scattering wave parameter, $S_{21}$1.

FIG. 6 is a circuit topology 290 for analog peak-to-peak detection of $S_{21}$. It is based on the use to two sequential sample and hold amplifiers 270 and 272 for peak detection. The magnitude of $S_{21}$ as a function of time serves directly as the imput 280 to peak detector 270 and after inversion by operational amplifier 274 to the input of the second peak detector 272. The peak detector outputs 282 and 284 are applied to a differential amplifier 276, after peak detector output 284 is inverted by operational amplifier 275. Status output 278 indicates updating of the tracking sample and hold.

What is claimed is:

1. Apparatus for cardiac hemodynamic monitoring, comprising
   (a) flexible transmitting antenna means adapted for mounting adjacent to the back of a patient;
   (b) transmitter means connected with said transmitting antenna means for generating a signal having a frequency between 900 and 930 MHz which is transmitted by said transmitting antenna means through the mediastinum of the patient, said signal being altered as a function of cardiac hemodynamic operation;
   (c) receiving antenna means adapted for mounting adjacent to the chest of the patient for receiving said altered signal, said transmitting and receiving antenna means providing close coupling to the chest wall of the patient;
   (d) means connected with said receiving antenna means for processing said received signal to produce outputs representing the magnitude and phase angle, respectively, of a bistatic scattering parameter ($S_{21}$) as functions of time on a heartbeat by heartbeat basis; and
   (e) display means for displaying said outputs representing the magnitude and phase angle of said bistatic scattering parameter to provide a visual indication of cardiac hemodynamic operation.

2. Apparatus as defined in claim 1, wherein said transmitting and receiving antenna means each comprise
   (1) a microstrip antenna; and
   (2) a passivation device comprising a thin randome of low inertia and low profile surrounding the microstrip antenna.

3. Apparatus as defined in claim 1, wherein said transmitting and receiving antenna means are portable, and further comprising an equipment vest containing said transmitting and receiving antenna means for mounting said antenna means on the patient.

4. Apparatus as defined in claim 1, wherein said processing means comprises a homodyne receiver with quadrature in-phase outputs.

* * * * *